United States Patent [19]

Jess

[11] 4,004,587
[45] Jan. 25, 1977

[54] PARENTERAL LIQUID ADMINISTRATION SET WITH NON-AIR BLOCKING FILTER

[75] Inventor: Thurman Sheldon Jess, Mundelein, Ill.

[73] Assignee: Baxter Travenol Laboratories, Inc., Deerfield, Ill.

[22] Filed: June 13, 1975

[21] Appl. No.: 586,665

[52] U.S. Cl. .............................. 128/214 R; 55/159; 128/214 C; 210/DIG. 23; 210/314
[51] Int. Cl.² ........................................... A61M 5/16
[58] Field of Search ........ 128/214 R, 214 C, 214.2; 210/DIG. 23, 314, 490; 55/159

[56] References Cited

UNITED STATES PATENTS

| | | | |
|---|---|---|---|
| 3,520,416 | 7/1970 | Keedwell | 210/490 |
| 3,631,654 | 1/1972 | Riely et al. | 55/159 |
| 3,854,907 | 12/1974 | Rising | 55/159 |

Primary Examiner—Dalton L. Truluck
Attorney, Agent, or Firm—Garrettson Ellis; Paul C. Flattery

[57] ABSTRACT

A parenteral liquid administration set is provided which comprises flexible tubing, connection means with a parenteral liquid source at one end of the tubing, and means for connection to a blood vessel-penetrating member, such as a needle, at the other end of the tubing. In accordance with this invention, a filter, positioned in fluid communication with the bore of the tubing, comprises a housing, which carries first and second filter members in parallel flow position so that each increment of fluid flow through the tubing passes through one or the other of the filter members. The first filter member is hydrophilic, to permit the passage of solution under normal administration conditions. The second filter member is hydrophobic, to permit the passage of gas after wetting of the filter members. Accordingly, the filter members, which are closed from the exterior by the administration set, cannot airblock by the accumulation of air bubbles immediately upstream of the filter members.

10 Claims, 4 Drawing Figures

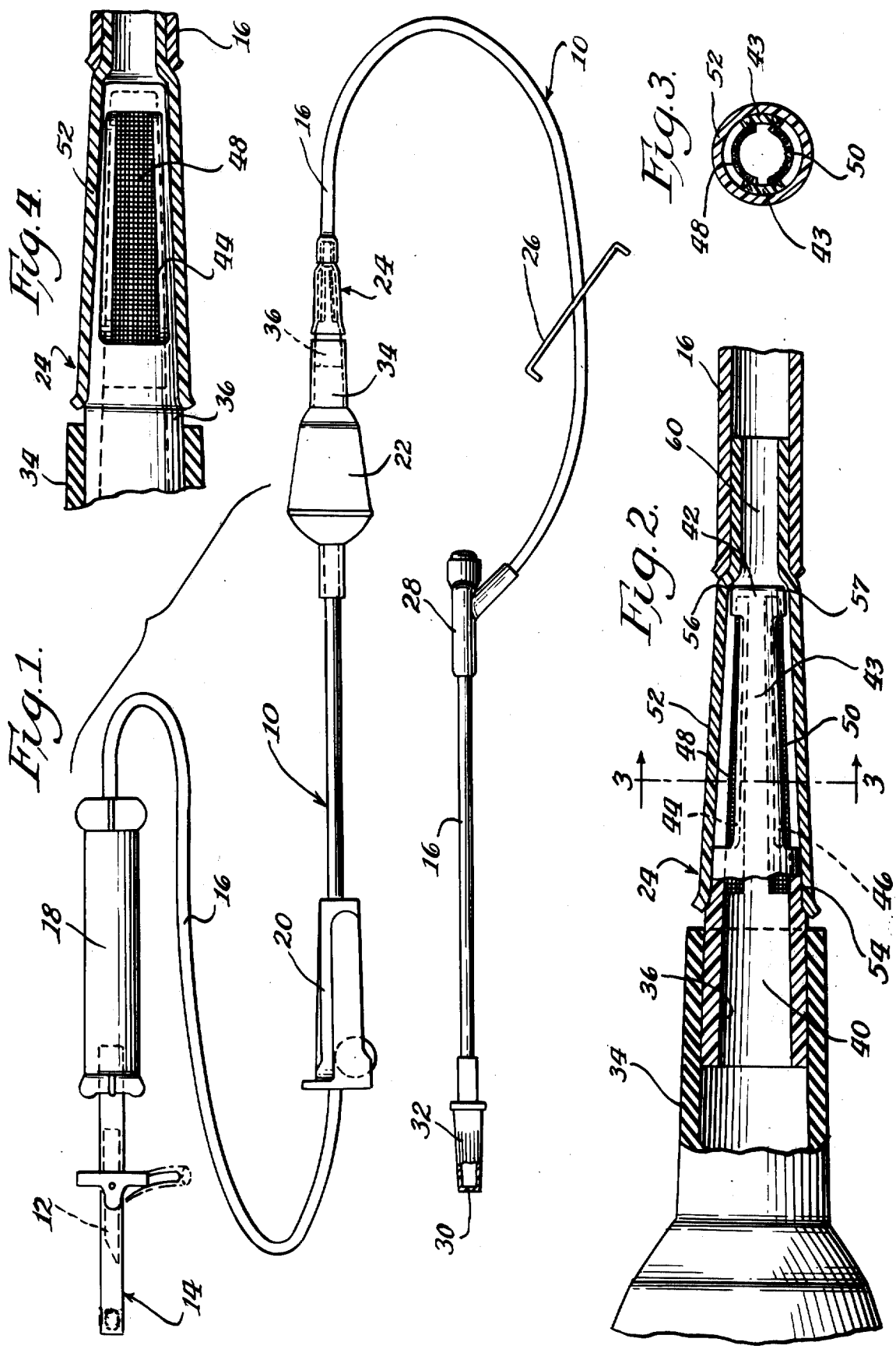

PARENTERAL LIQUID ADMINISTRATION SET WITH NON-AIR BLOCKING FILTER

BACKGROUND OF THE INVENTION

Parenteral liquid administration sets are utilized for administering blood, or parenteral solutions such as normal saline, normal glucose, Ringers solution, or the like, typically into the vein of a patient.

It is long been known that foreign particulate material, particularly that having a particle size of above five microns, is highly undesirable for administration. However, inevitably, small amounts of such particulate material are found in extracorporeal blood and parenteral solutions. Because of this, blood has long been passed through a filter in its administration set, immediately prior to infusion in the patient.

At the present time, there is also growing interest in the filtration of other parenteral solutions immediately prior to administration, to remove particulate material.

Blood filters must have a pore size large enough to allow blood cells to pass. However, when filters for solutions having smaller pore sizes, on the order of 5 microns or less, are used, the problem of "air-blocking" can arise. This occurs when, as the set is being primed by aqueous parenteral solution, the aqueous liquid comes into contact with the 5 micron filter before all of the air upstream of the filter has passed through it. If such a filter is hydrophilic in nature, as such filters generally must be in order to pass aqueous liquids, wetting of the filter will tend to prevent the passage of air.

Accordingly, the air accumulates in a large bubble behind the filter until it frequently stops flow of liquid through the filter. If this happens, the solution administration set is disabled until the user manages to force the air through the filter by pressure, or the set is disconnected from the parenteral solution source, and the air bubbles shaken out of the inlet of the set. This latter expedient is an undesirable and non-sterile procedure.

Frequently, in case of air-blocking, the entire set must be discarded and another set primed for use.

In the prior art, it has been suggested in Keedwell U.S. Pat. No. 3,520,416 to prepare a microporous filter for parenteral solution sets in which certain portions of a hydrophilic filter material are rendered hydrophobic by the application of a silicone material or the like, in a pattern of repeating stripes or dots, etc. However, this suggestion has the significant disadvantage that it is impractical for use with the very small filters which are desirable for use with the typical, commercial parenteral solution administration sets.

For example, it is generally unnecessary for the overall area of the filter in the set to be even as much as one square centimeter. Usually, the total filter surface area can be about 0.6 square centimeter.

In attempting to use the Keedwell solution to the problem of air-blocking, it becomes very difficult to precisely control the exact ratio of the area of silicone-treated filter membrane to the area of untreated hydrophilic membrane area in the manufacture of such a small filter. Accordingly, mass-produced solution administration sets having filters that attempt to utilize the Keedwell invention may have substantially variable performance, because of the difficulty of precisely controlling the ratio of silicone-treated areas to the untreated hydrophilic areas, when the total filter surface area is less than a square centimeter.

Also, it is not possible for the hydrophobic and hydrophilic filter filter portions, in Keedwell, to have different pore sizes or to be made from different basic materials. This reduces the flexibility of use and design of structures incorporating that invention.

It is also known in patents such as Rosenberg U.S. Pat. Nos. 3,523,408 and Riely, et al. Pat. No. 3,631,654 to provide a filter having separate pieces of hydrophobic and hydrophilic filter material. However, in these devices, the hydrophobic filter members are exposed to the exterior. Accordingly, breakage of the hydrophilic filter member can cause, in conjunction with a suction pressure head of an administration set, the suction of exterior air into the administration set downstream from the filter. If a pump is utilized for pressure administration of liquid to a patient, the results of this can be fatal, since the sucked air can be directly pumped into the patient.

By the invention of this application, a filter for an I. V. administration set is provided in which the ratio of hydrophobic filter area to hydrophilic filter area can be precisely and routinely controlled on a mass production basis. Also, the pore sizes of the respective filter materials can be individually selected to be of the exact, desired size for optimum functioning for the intended purpose. Similarly, the filter is safe in the event of rupture of the filter members for any reason, since the filter members are closed from the exterior. Accordingly, a defective filter will result in no injury, and will merely fail, to a greater or lesser extent, in its filtering function.

DESCRIPTION OF THE INVENTION

In accordance with this invention, a parenteral liquid administration set is provided which comprises flexible tubing, means such as a spike for connection of the set with a parenteral liquid source at one end of the tubing, means such as a needle hub for connection of the set to a blood vessel-penetrating member at the other end of the tubing, and a filter positioned in communication with the bore of the tubing of the set.

In accordance with this invention, the filter in the set comprises a housing. The housing carries a first filter member and a separate, second filter member in a parallel flow position so that each increment of fluid flow through the tubing bore passes through one (or the other) of the filter members.

The first filter member is hydrophilic in nature, to permit the passage of aqueous liquid such as parenteral solution under normal parenteral liquid administration conditions. The second filter member is hydrophobic in nature, to permit the passage of gas after the filter members have been in contact with aqueous liquid, and accordingly the first hydrophilic filter member may no longer allow air to pass. As a result, air-blocking of the filter is prevented, since air can continue to pass through the hydrophobic filter member even when the hydrophilic filter member blocks it after wetting.

As previously stated, the filter members are closed from the exterior by the administration set, resulting in increased safety, when compared with structures having exposed hydrophobic filter members.

Generally, the first and second filter members utilized herein each define an area of less than 0.5 square centimeter. Typically, the area defined for each of the first and second filter members is each about 0.3 square centimeter.

The housing itself may be positioned within the bore of the flexible tubing and essentially be closed from the exterior.

If desired, the first filter member defines pores which are of a different size from pores defined in the second filter member. For example, the first filter member may have pores of 1 to 5 microns measured by the minimum size of the particles retained, while the second filter member may have the same pore size, or less, by the same measurement. For example, the filter members may have a pore size of 3 microns for the first filter member and 1.5 microns for the second filter member.

This present invention can also be used in other fluid flow apparatus besides parenteral liquid administration sets, for example, in ampules for filtration of contents being withdrawn or added without air-blocking, in syringes and hollow needles for the same purpose, or in any desired non-medical use.

In the drawings,

FIG. 1 is an elevational view of a solution administration set, utilizing the invention of this application.

FIG. 2 is a greatly enlarged, fragmentary elevational view, with portions broken away, of the filter of this invention utilized in the administration set of FIG. 1.

FIG. 3 is a sectional view taken along line 3—3 of FIG. 2.

FIG. 4 is an elevational view similar to FIG. 2, but rotated about its long axis by 90°, with certain portions broken away.

Referring to the drawings, a typical administration set 10 for parenteral solutions is provided. Spike 12, covered with a conventional sterile closure 14, is provided at one end of a length of flexible tubing 16 for use as a connection means with a parenteral solution source, for example any commercially available solution bottle or bag.

Spike 12 is in fluid communication with the interior of a conventional drip chamber 18, for measuring the rate of flow of liquid through the administration set. A conventional roller clamp 20 is provided as indicated to provide the usual flow control function necessary in administration sets. A latex bulb 22 interrupts tube 16, and is in fluid communication therewith, to act as a supplemental medication injection site.

Filter 24 is then positioned with its upstream end in communication with bulb 22 and its downstream end in communication with a continuation of flexible tubing 16.

If desired, a slide clamp 26 can be provided, for further flow control in the position indicated, and a Y-connection or another junction means 28 may be provided for connection with another administration set, for further administration of supplemental medication, other fluids, or the like.

At the other end of tubing 16 is a needle hub 30 for receiving a vein-puncturing needle for establishing fluid communication with the patient's venous system. Hub 30 is shown to be surrounded by a conventional sterile cover 32, which is shown herein to be broken away in portions to exhibit hub 30.

Referring more particularly to FIGS. 2 through 4, a detailed view of the filter 24 of this invention is shown. The downstream, elongated end 34 of a latex bulb 22 is attached to a first housing member 36 in any conventional manner. First housing member 36 is shown to be a generally tubular member defining bore 40. Bore 40 is closed at its downstream end by wall 42.

First housing member 36 defines, between longitudinal sections 43, adjacent its downstream end, a pair of longitudinally-extending windows 44, 46 which are positioned in diametrically opposite relation to each other. First and second filter members 48, 50 are each positioned in a longitudinally extending window, in peripherally sealed relation thereto, so that fluid cannot flow through windows 44, 46 without passing through their respective filter members 48, 50. The structure can be manufactured by molding, with the peripheries of filter members 48, 50 becoming integrally fused with the structure of first housing member 36, which may be made of a thermoplastic material. As shown, first, hydrophilic filter member 48 occupies window 44, and second, hydrophobic filter member 50 occupies window 46.

Hydrophilic membrane 48 may comprise a copolymer of polyvinyl chloride and acrylonitrile placed on a nylon fabric substrate, and having an effective pore size of five microns (i.e. the membrane is capable of preventing the passage of 90 percent of 5 micron particles). This material is sold by the Gelman Instrument Company of Ann Arbor, Mich., under the designation AN 5000.

Hydrophobic membrane 50 may be a similar material to the above, having the same pore size, but treated with an organosilicon compound to render it hydrophobic. Such material is sold by the Gelman Instrument Company under the designation ANH 5000.

Alternatively, a hydrophobic membrane material can be used which is similar to the above, but has an effective pore size of three microns (i.e. capable of retaining 90 percent or more of three micron particles).

If larger surface areas for the filter members 48, 50 are used, then smaller pore sizes can be used, while still exhibiting the desired flow rates for the typical administration set.

It is also contemplated that, in the configuration shown, in which each of filter members 48, 50 has a surface area of about 0.3 square centimeter, that the effective pore size of hydrophilic membrane 48 may be reduced to about three microns, if desired, and the effective pore size of hydrophobic membrane 50 can be reduced to about 1.5 microns, if desired.

Also, hydrophobic membrane 50 may be made out of porous polytetrafluroethylene membrane having pores sized in the micron range. Such material is made by W. L. Gore and Associates of Newark, Del. under the trademark GORE-TEX.

Second tubular housing member 52 is positioned as shown in the drawings about the downstream end of first housing member 36, to close filter members 48, 50 from the exterior, except through communication by way of the interior of administration set 10 to an end thereof. Second housing member 52 may be sealed to first housing member 36 by solvent or heat sealing at cylindrical connection area 54. The respective housings are so proportioned as to provide apertures 56, 57 adjacent wall 42 and exterior to first and second filter members 48, 50, to complete a flow path through filter 24, including bulb 22, bore 40, filters 48 or 50, apertures 56 or 57, and from there out of bore 60 of second housing member 52 and again into tubing 16. Tubing 16 is attached to the downstream end of second housing member 52.

As illustrated, filter members 48, 50 are in parallel flow positions to each other, in that the flow through filter 24 branches into parallel, separate flow paths through the filter members. Accordingly, any given fluid increment passing through filter 24 must pass through either filter member 48 or 50, and correspondingly pass through aperture 56 or 57, then rejoining a common path downstream in bore 60 of the second housing member 52.

As a result of this, after hydrophilic filter 48 has been wetted, and no longer easily allows the passage of gas bubbles, the system will nevertheless not be subject to "air-block", because air and other gas bubbles can continue to pass through second filter member 50, so that filter 24 does not become filled with air, preventing the further passage of liquids therethrough. Accordingly, the set of this invention may utilize an ultrafine filter having a pore size of down to 5 microns or even less, without encountering the serious priming problems which are usually found in solution administration sets which contain an ultrafine filter.

Air can pass through the set, to permit the set to be completely primed, being drained of its air and replaced with solution prior to connection with the patient's venous system. The ultrafine filtration of the parenteral solution can prevent the injection of particulate matter of any desired minimum size into the patient, depending upon the pore size of the filter.

As a result of this, improved parenteral solution therapy can be provided to the patient by means of the set of this invention, in that, for the first time, a safe, easily-primed solution administration set is provided which can, at the same time, give the final filtration of solutions deemed by many to be most desirable, when it can be obtained without encountering the serious difficulties in priming the enclosed-filter sets of the prior art.

The above has been offered for illustrative purposes only, and is not intended to limit the scope of the invention of this application, which is as defined in the claims below.

That which is claimed is:

1. In a fluid flow apparatus which comprises a flow conduit means adapted for connection to a liquid source, and a filter positioned in communication with said flow conduit, the improvement comprising, in combination:

said filter comprising a housing, said housing carrying a first filter member and a separate, second filter member, in parallel flow position, whereby each increment of fluid flow through said flow conduit passes through one of said filter members, said first filter member being hydrophilic in nature to permit passage of aqueous liquid under normal liquid administration conditions, said second filter member being hydrophobic in nature to permit the passage of gas after said filter members have been in contact with aqueous liquid, whereby air-blocking of said filter is prevented, said filter members being closed from the exterior, and physically spaced from each other.

2. The parenteral liquid administration set of claim 1 in which said housing comprises a tubular member defining a pair of longitudinally extending windows positioned in diametrically opposite relation to each other, said first and second filter members being each positioned in a said longitudinally extending window in peripherally sealed relation thereto, whereby a path of fluid flow extends through the interior of said tubular housing, through said windows and said filter members, and through the bore of said tubing.

3. The fluid flow apparatus of claim 1 in which the pore size of said second filter member is less than the pore size of said first filter member.

4. The apparatus of claim 1 in which said filter is mounted in a parenteral liquid administration set.

5. The parenteral liquid administration set of claim 7 in which said housing comprises a tubular member defining a pair of longitudinally extending windows positioned in diametrically opposite relation to each other, said first and second filter members being each positioned in a said longitudinally extending window in peripherally sealed relation thereto, whereby a path of fluid flow extends through the interior of said tubular housing, through said windows and said filter members, and through the bore of said tubing.

6. In a parenteral liquid administration set which comprises tubing, means for connection of said set with a parenteral liquid source at one end of said tubing, means for connection of said set to a blood vesselpenetrating member at the other end of said tubing, and a filter positioned in communication with the bore of said tubing, the improvement comprising, in combination:

said filter comprising a housing, said housing carrying a first filter member, and a separate, second filter member, in parallel flow position whereby each increment of fluid flow through said bore passes through one of said filter members, said first filter member being hydrophilic in nature to permit the passage of aqueous liquid under normal parenteral liquid administration conditions, said second filter member being hydrophobic in nature to permit the passage of gas after said filter members have been in contact with aqueous liquid, whereby air-blocking of said filter is prevented, said filter means being closed from the exterior, and physically spaced from each other.

7. The parenteral liquid administration set of claim 6 in which said first and second filter member each define an area of less than 0.5 square centimeter.

8. The parenteral liquid administration set of claim 6 in which said housing comprises a tubular member defining a pair of longitudinally extending windows positioned in diametrically opposite relation to each other, said first and second filter members being each positioned in a said longitudinally extending window in peripherally sealed relation thereto, whereby a path of fluid flow extends through the interior of said tubular housing, through said windows and said filter members, and through the bore of said tubing.

9. The parenteral liquid administration set of claim 6 in which the pore size of said second filter member is less than the pore size of said first filter member.

10. In a fluid flow apparatus which comprises a flow conduit means adapted for connection to a liquid source and a filter positioned in communication with said flow conduit, the improvement comprising, in combination:

said filter comprising a housing, said housing carrying a first filter member, and a separate, second filter member, in parallel flow position, whereby each increment of fluid flow through said flow conduit passes through one of said filter members, said first filter member being hydrophilic in nature to permit passage of aqueous liquid under normal parenteral liquid administration conditions, said second filter member being hydrophobic in nature to permit the passage of gas after said filter members have been in contact with aqueous liquid, the pore size of said first filter member being from 1 to 5 microns, as measured by the minimum size of the particles retained, while said second filter member exhibits a pore size of less than the pore size of said first filter member, said filter members being closed from the exterior.

* * * * *